United States Patent [19]
Martin et al.

[11] Patent Number: 5,875,016
[45] Date of Patent: Feb. 23, 1999

[54] ASYMMETRICAL EYEWEAR

[75] Inventors: Brent R. Martin; Sean G. Sullivan, both of North Vancouver, Canada

[73] Assignee: Sentinel Importing Corporation, North Vancouver, Canada

[21] Appl. No.: 834,508

[22] Filed: Apr. 4, 1997

Related U.S. Application Data

[62] Division of Ser. No. 477,349, Jun. 7, 1995, Pat. No. 5,648,831.

[51] Int. Cl.$^6$ ................. G02C 1/00; G02C 5/14; G02C 5/12
[52] U.S. Cl. ................. 351/41; 351/111; 351/136
[58] Field of Search ................. 351/41, 44, 51, 351/52, 63, 111, 124, 136, 158; 2/454

[56] References Cited

U.S. PATENT DOCUMENTS 5,129,719  7/1992  Dombrosky .
5,633,692  5/1997  Schleger et al. ................. 351/44
5,648,831  7/1997  Martin et al. ................. 351/51

*Primary Examiner*—Hung Xuan Dang
*Attorney, Agent, or Firm*—Elbie R. de Kock

[57] ABSTRACT

Eyewear (10) comprises a frame (12) for housing a pair of eye lenses (14.1), (14.2) therein. The frame (12) has a bridge portion (16) for resting on a user's nose and a pair of temple members (18.1), (18.2) for locating the frame (12) in position on the head of a user. The temple members (18.1), (18.2), respectively, are pivotally connected by means of a pair of pivotal connections (19.1), (19.2) which are spaced from each other and located asymmetrically with respect to the bridge portion (16). In another embodiment (70) the frame (12) has a bridge portion (16) with opposing sides for resting on a user's nose, the opposing sides being asymmetrical with respect to each other. In a further embodiment the frame (12) has a bridge portion (16) with opposing sides and a nose pad (72), (74) on each of the opposing sides for resting on a user's nose, the nose pads (72), (74) being located at different positions on the respective sides of the bridge portion (16).

10 Claims, 5 Drawing Sheets

ASYMMETRICAL EYEWEAR

CROSS REFERENCE TO RELATED APPLICATION

This application is a division of U.S. patent application Ser. No. 08/477,349 filed Jun. 7, 1995 now U.S. Pat. No. 5,648,831, the entire contents of which is incorporated herein by reference.

FIELD OF THE INVENTION

This invention relates to eyewear of the type which comprises a frame for supporting a pair of eye lenses and which is supported on the head of the user by means of a pair of temple members which are pivotally connected to the frame. In particular, but not exclusively, the invention relates to protective eyeglasses which is suitable for use in sports or recreational activities, such as snowboarding or surfboarding.

BACKGROUND OF THE INVENTION

In sports activities, such as snowboarding, protective sunglasses are worn to protect the user's eyes from the wind and glare of the sun. It is often a problem in such an application that one lens of the eyewear will become fogged up, thereby restricting the vision of the user. In addition, such eyewear does not provide proper protection against wind.

It is one of the objects of the present invention to alleviate the above mentioned difficulties.

SUMMARY OF THE INVENTION

According to the invention there is provided eyewear comprising a frame for housing a pair of lenses therein, the frame having a bridge portion for resting on a user's nose and a pair of temple members for locating the frame in position on the head of a user, the frame including lens retaining portions, each said lens retaining portion comprising a pair of spaced frame portions for receiving the respective lens therebetween, said lens retaining portions extending from the bridge portion of the frame in opposite directions away from the bridge portion and wherein one of said lens retaining portions is larger than the other one of said lens retaining portions being non-planar for extending at least partially around the side of a user's face.

Also according to the invention there is provided eyewear comprising a frame for housing a pair of lenses therein, the frame having a bridge portion for resting on a user's nose and a pair of temple members for locating the frame in position on the head of a user, wherein one of said temple members is longer than the other one of said temple members.

Further according to the invention there is provided eyewear comprising a frame for housing a pair of eye lenses therein, the frame having a bridge portion for resting on a user's nose and a pair of temple members for locating the frame in position on the head of a user, said temple members being pivotally connected by means of a pair of pivotal connections which are spaced from each other and wherein the pivotal connections are located asymmetrically with respect to said bridge portion.

Also according to the invention there is provided eyewear comprising a frame for housing a pair of eye lenses therein, the frame having a bridge portion for resting on a user's nose and lens retaining portions, each said lens retaining portion comprising a pair of spaced frame portions for receiving the respective lens therebetween, said lens retaining portions extending curvilinearly from the bridge portion of the frame in opposite directions away from the bridge portion for extending at least partially around the side of a user's face and wherein the radius of curvature of the one of said lens retaining portions differs from the other.

Further according to the invention there is provided eyewear comprising a frame for housing a pair of lenses therein, the frame having a bridge portion having opposing sides for resting on a user's nose, wherein said opposing sides are asymmetrical with respect to each other.

Also according to the invention eyewear comprising a frame for housing a pair of lenses therein, the frame having a bridge portion having opposing sides and a nose pad on each of said opposing sides for resting on a user's nose, wherein the nose pads are located at different positions on the respective sides of the bridge portion.

Also according to the invention there is provided eyewear comprising a frame for housing a pair of lenses therein, the frame having a bridge portion for resting on a user's nose and a ventilation opening in said bridge portion having a pair of opposing side walls which are at an angle with respect to the forward direction for directing air flowing through said ventilation opening in a predetermined direction.

Further objects and advantages of the invention will become apparent from the description of a preferred embodiment of the invention below.

BRIEF DESCRIPTION OF THE DRAWINGS

The invention will now be described, by way of an example, with reference to the accompanying drawings, in which.

DETAILED DESCRIPTION OF PREFERRED EMBODIMENT

Figure 1:
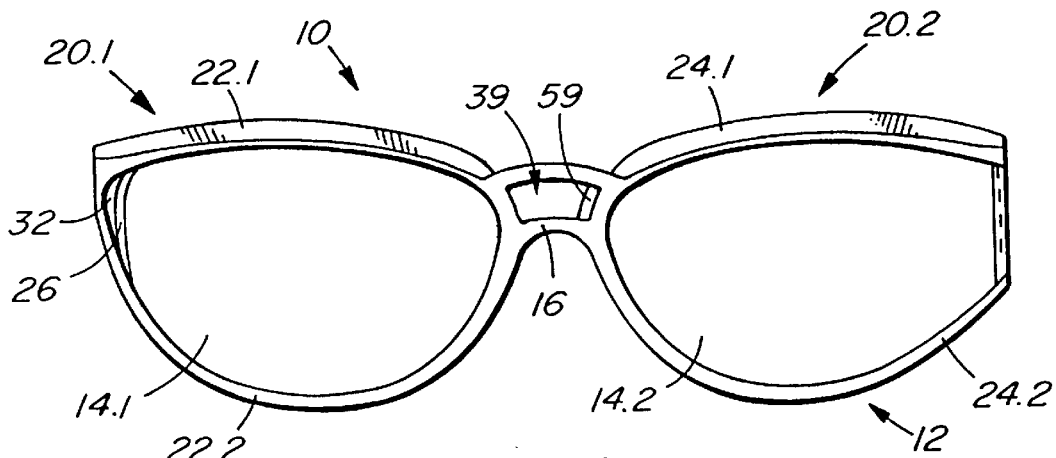
FIG. 1 is a front view of sunglasses according to one embodiment of the invention.

In FIGS. 1 to 4, reference numeral 10 generally indicates a pair of sunglasses according to the invention. The glasses 10 comprise a frame 12 provided with a pair of lenses 14.1 and 14.2 therein. The frame 12 has a bridge portion 16 for resting on a user's nose and a pair of temple members 18.1 and 18.2 as provided for locating the frame 12 in position on the head of a user. The temple members 18.1, 18.2 are connected to the frame 12 through pivotal connections 19.1 and 19.2, respectively. It can be seen that the position of the pivotal connections 19.1 and 19.2 are asymmetrical with respect to the position of the bridge portion 16.

Figure 2:
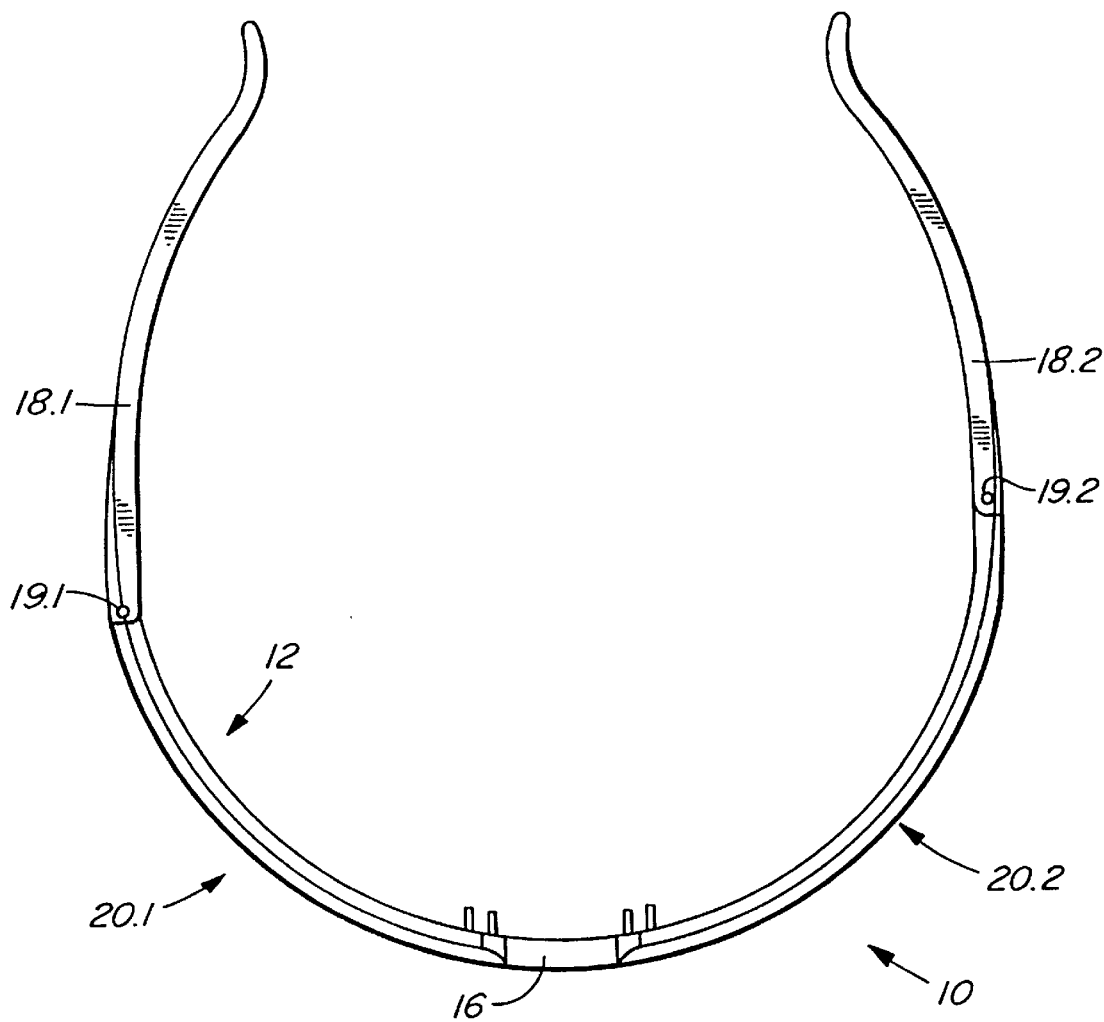
FIG. 2 is a plan view of the sunglasses of FIG. 1.

As can be seen further from FIG. 2, the frame 12 extends curvilinearly from the temple member 18.1 to the temple member 18.2.

The frame 12 comprises lens retaining portions 20.1 and 20.2 for respectively, holding the lenses 14.1 and 14.2 in position. The lens retaining portion 20.1 comprises a pair of spaced frame portions 22.1 and 22.2 extending from the pivotal connection 19.1 to the bridge portion 16 for receiving the lens 14.1 therebetween. Likewise, the lens retaining portion 20.2 comprises a pair of spaced frame portions 24.1 and 24.2 extending from the pivotal connection 19.2 to the bridge portion for receiving the lens 14.2 therebetween.

As can be seen, particularly from FIG. 2, the lens retaining portion 20.2 is longer than the lens retaining portion 20.1. The lens 14.2 is longer than the lens 14.1. When worn on the head of a user, the lens retaining portions 20.1, 20.2, and in particular the lens retaining portion 20.2, will "wrap around" the side of the face. Thus, the glasses 10 provide a more effective wind shield for the side of the face of a user which is turned into the wind, during snowboarding, for example.

The glasses 10 in the present example are for a regular user which would have the left foot forward on the snowboard so that the left side of the face would be turned into the wind. For a so-called "goofy foot" user, where the right foot would be forward and the right side of the face turned into the wind, the glasses would be a mirror image of the glasses 10, i.e. it would be the lens 14.1 and the lens retaining portion 20.1 which would be larger.

In order to counteract the lenses 14.1 and 14.2 from fogging up on the inside, ventilation means is provided for allowing air to enter into the area behind the lenses 14.1 and 14.2. In the present example, the ventilation means comprises an opening provided between one end of the lens 14.1 and the frame 12, as shown at 26 in FIGS. 1 and 3, and slots provided in the frame 12 adjacent to the lens 14.2, as indicated at 30 in FIG. 4. Alternatively or in addition, the ventilation means may comprise openings which are provided in the lenses themselves.

The opening 26 can be provided by simply making the lens 14.1 somewhat shorter than the lens retaining portion 20.1 to leave a gap which forms the opening 26. Reference numeral 32 adjacent to the opening 26, indicates an indent in the frame 12. Reference numeral 36 in FIG. 4 indicates an indented lens retaining rim for receiving and supporting the end of the lens 14.2 and reference numeral 38 indicates rim support members for supporting the lens retaining rim 36.

A further ventilation opening 39 is provided in the bridge portion 16, as shown in FIG. 1.

Figure 3:
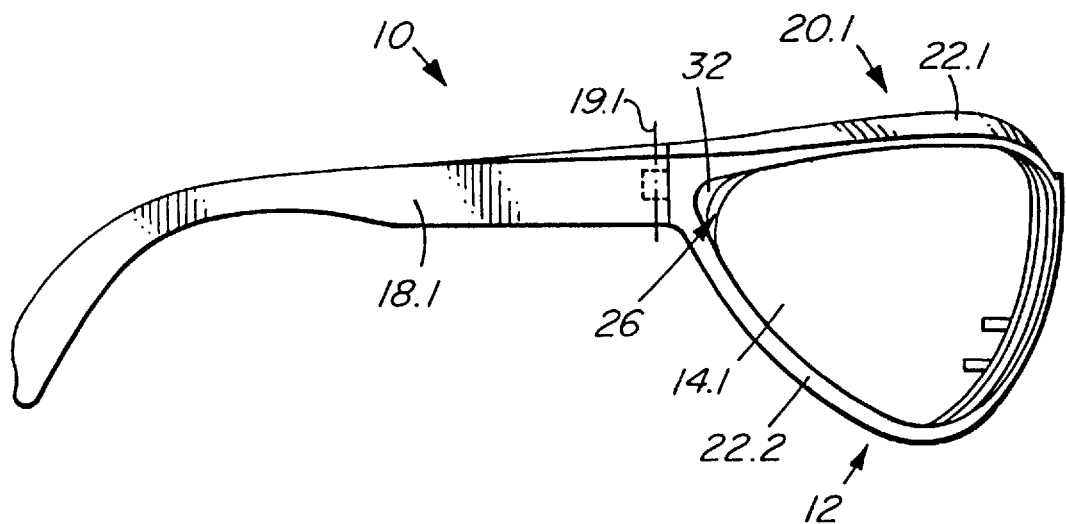
FIG. 3 is a right side view of the sunglasses of FIG. 1.
Figure 4:
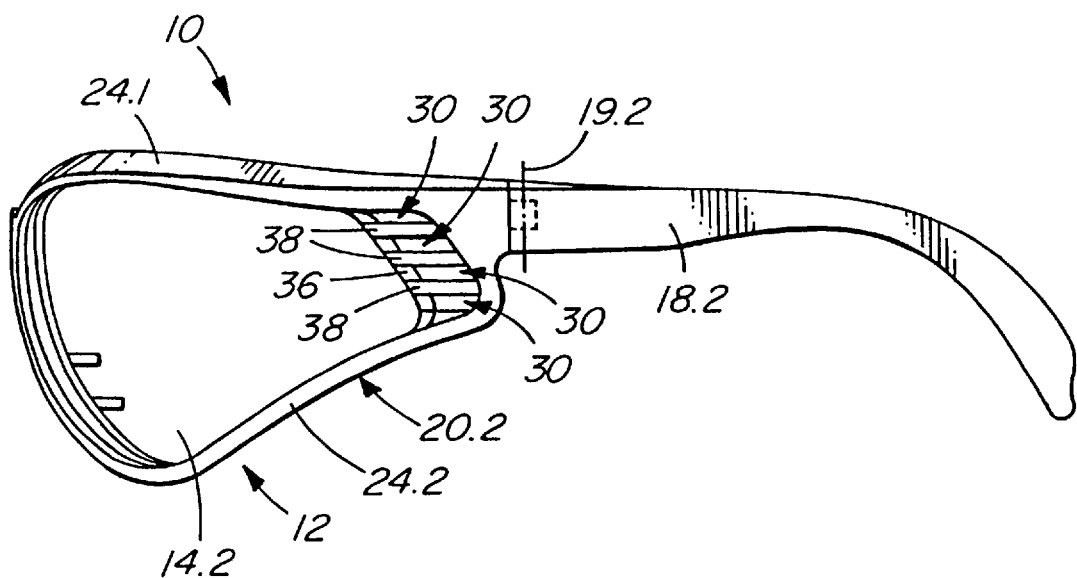
FIG. 4 is a left side view of the sunglasses of FIG. 1.

As a result of the fact that the lens retaining portion 20.2 is longer than the lens retaining portion 20.1, the temple member 18.2 is shorter than the temple member 18.1, as shown in FIGS. 2 to 4.

In use, the sunglasses 10 will provide added protection to the eye of a user which is turned into the wind during a sporting activity, such as snowboarding, due to the longer length of the lens covering that particular eye. In addition the lenses 14.1 and 14.2 are counteracted from fogging up due to the ventilation means provided.

The lens retaining portions 20.1 and 20.2 may be detachable from each other so that, for example, the portion 20.2 with the temple member 18.2 can be removed from the portion 20.1 and replaced with another lens retaining portion which is symmetrical with the portion 20.1. In this way, the asymmetrical sunglasses 10 can be temporarily converted into a symmetrical pair and visa versa.

Although the example described above relates to sunglasses for use in sports such as snowboarding or surfboarding, it will be appreciated that the invention can also be applied to other types of eyeglasses, such as weather goggles, for example.

Figure 5:
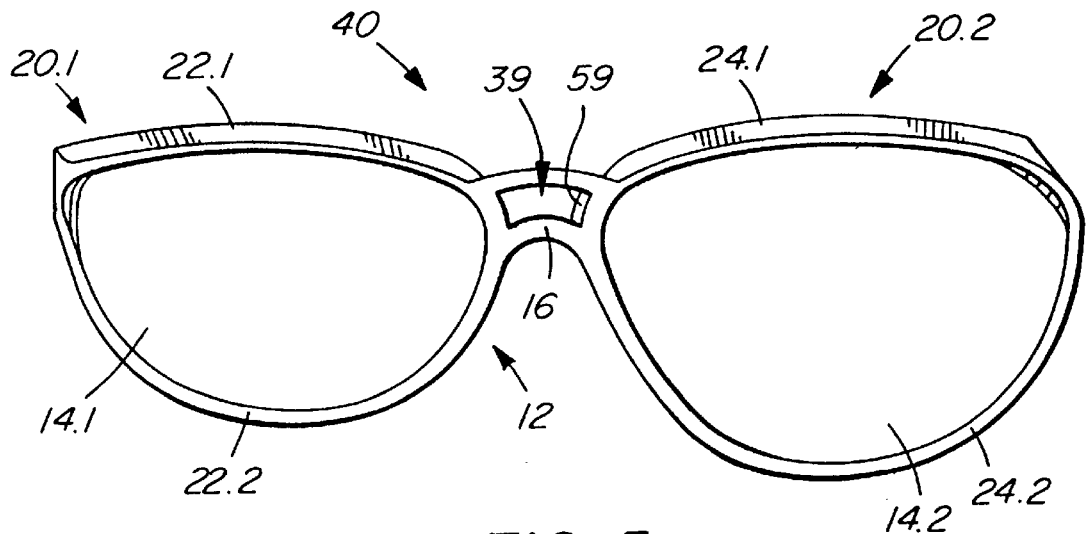
FIG. 5 is a front view of sunglasses according to another embodiment of the invention.
Figure 6:
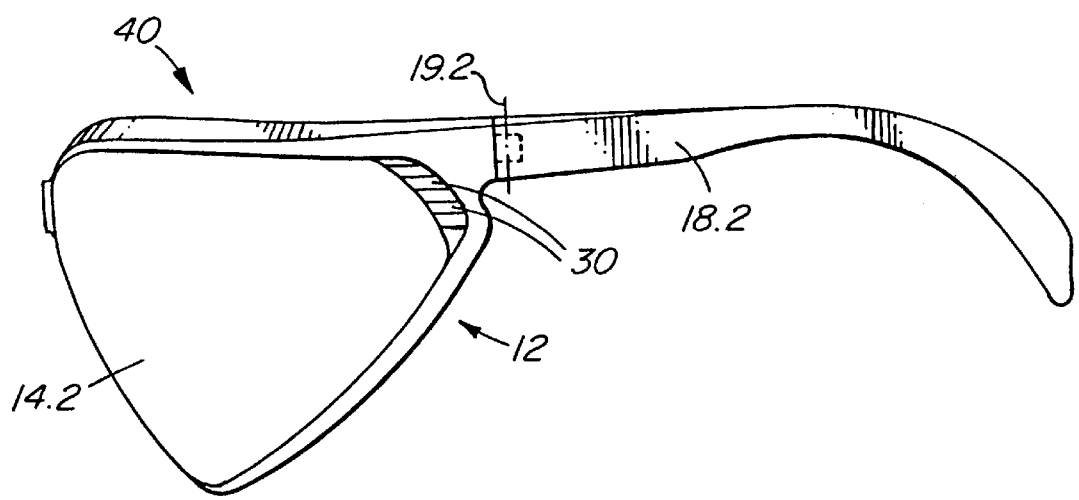
FIG. 6 is a left side view of the sunglasses of FIG. 5.
Figure 7:
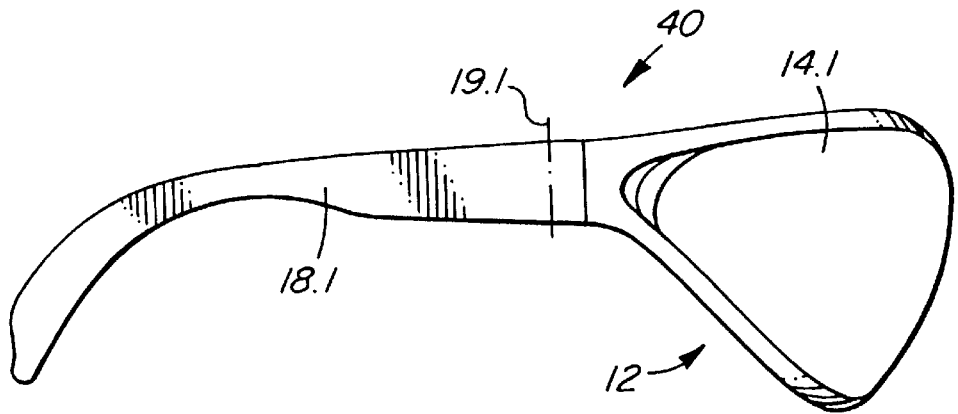
FIG. 7 is a right side view of the sunglasses of FIG. 5.

With reference to FIGS. 5 to 7, sunglasses 40 according to another embodiment of the invention is shown. The glasses 40 also comprise a frame 12 with bridge portion 16 and temple members 18.1, 18.2 connected to the frame 12 by means of pivotal connections 19.1 and 19.2, respectively. The glasses 40 also include lenses 14.1 and 14.2 supported between spaced frame portions 22.1, 22.2 and 24.1, 24.2 of lens retaining portions 20.1 and 20.2, respectively.

In this embodiment it can be seen that the lens 14.2 is not only longer in the horizontal direction, as is the case with the sunglasses 10, but it is also longer or wider in the vertical direction.

As is clear from the side views shown in FIGS. 6 and 7, both lenses 14.1 and 14.2 will wrap around the eyes of a user, but the lens 14.2 does so to a greater extent than the lens 14.1 to provide better protection when used in a sport not involving full frontal activity but where one side of the face is turned into the direction of movement.

Figure 8:
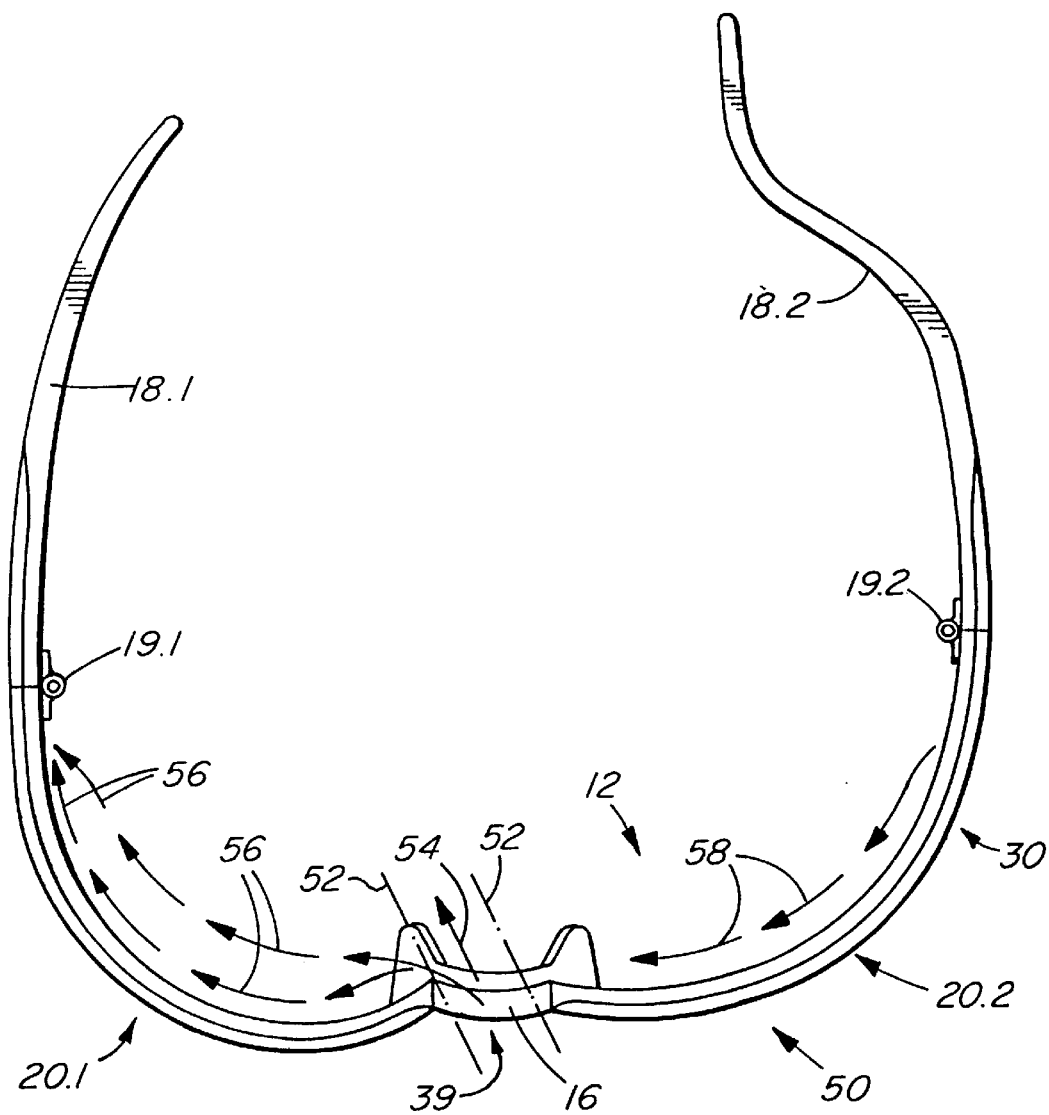
FIG. 8 is a plan view of sunglasses according to another embodiment of the invention.

With reference to FIG. 8, sunglasses 50 according to a further embodiment of the invention is shown. Again as in the previous embodiments, like reference numerals are used to indicate corresponding parts.

In this embodiment, the curvatures of the lens retaining portions 20.1 and 20.2 holding the lenses 14.1 and 14.2 are not equal. The lens retaining portion 20.1 and lens 14.1 have a greater curvature than the lens retaining portion 20.2 and lens 14.2. The lens 14.2 wraps around the side of the face of a user to a greater extent than the lens 14.1.

Also the vertical sides of the ventilation opening 39 are angled with respect to the forward direction and coincide with a plane indicated by the lines 52. Thus, air entering through the ventilation opening 39 will be diverted sideways as shown by the arrow 54 to provide ventilation for the lens 14.1, as indicated by the arrows 56. Air entering through the ventilation openings 30 provide ventilation for the lens 14.2, as indicated by the arrows 58. This counteracts the lenses 14.1 and 14.2 from being fogged-up.

The angled aspect of the opening 39 is also present in the embodiments of FIGS. 1 and 5, the slanted left vertical side being indicated at 59. The same aspects of ventilation as described above also apply to these embodiments.

A further aspect of the sunglasses 50 is that the temple member 18.2, which is the shorter in the sunglasses 10 and 40, is in fact longer in this embodiment and curved inwardly to provide a better grip.

Figure 9:
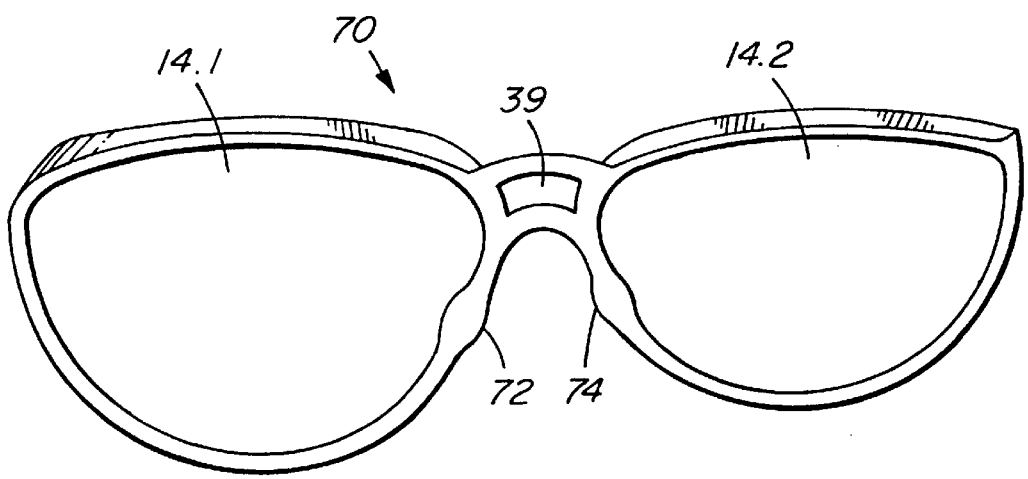
FIG. 9 is a front view of sunglasses according to a further embodiment of the invention.

In FIG. 9, yet a further embodiment of the sunglasses 70 is shown. The sunglasses 70 is an example of the glasses that would be used by a so-called "goofy foot" user, referred to above, where the lens 14.1 is the larger. In this embodiment the ventilation opening 39 is asymmetrical.

The glasses 70 also include nose pieces 72 and 74 arranged so that the nose piece 74 on the smaller lens 14.2 is located higher than the nose piece 72.

Figure 10:
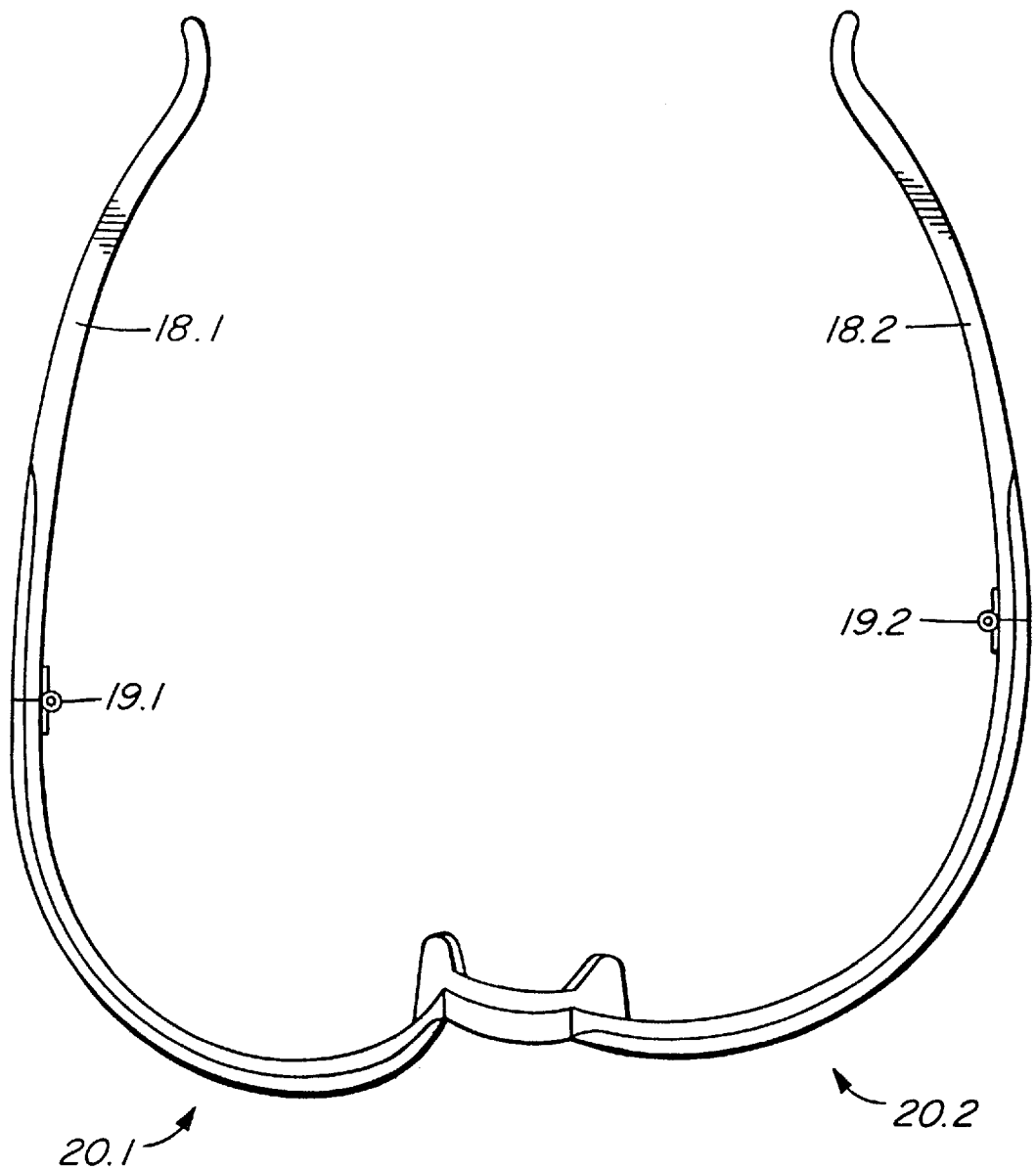
FIG. 10 is a plan view of sunglasses according to yet another embodiment of the invention.

With reference to FIG. 10, sunglasses 80 according to a further embodiment of the invention is shown. In this embodiment the curvatures of the portions 20.1 and 20.2 are again different and the portion 20.1 curves deeper towards the bridge portion 16 than the portion 20.2. As seen from above, the frame of the ventilation opening 39 is angled with respect to the forward direction as shown, again to direct air flowing through the opening 39 towards one lens.

While only preferred embodiments of the invention have been described herein in detail, the invention is not limited thereby and modifications can be made within the scope of the attached claims.

What is claimed is:

1. Eyewear comprising a frame for housing a pair of lenses therein, the frame having a bridge portion having opposing sides for resting on a user's nose, wherein said opposing sides are asymmetrical with respect to each other.

2. Eyewear comprising a frame for housing a pair of lenses therein, the frame having a bridge portion having opposing sides and a nose pad on each of said opposing sides for resting on a user's nose, wherein the nose pads are located at different positions on the respective sides of the bridge portion.

3. Eyewear comprising a frame for housing a pair of eye lenses therein, a pair of temple members hinged to the frame at opposite ends of the frame and spaced at unequal distances from a non-hinged bridge portion which is located between said opposite ends of the frame.

4. The eyewear according to claim 3 or 1 or 2, wherein said frame includes lens retaining portions for housing the lenses, each said lens retaining portion comprising a pair of spaced frame portions for receiving the respective lens therebetween, said lens retaining portions extending from the bridge portion of the frame in opposite directions away from the bridge portion and wherein one of said lens retaining portions is larger than the other lens retaining portion.

5. The eyewear according to claim 4, including a pair of lenses housed in the frame, and wherein the lens housed in the larger lens retaining portion is larger than the lens housed in the other lens retaining portion.

6. The eyewear according to claim 5, wherein the eyewear comprises sunglasses.

7. The eyewear according to claim 4, wherein at least said larger one of said lens retaining portions is curved for extending at least partially around the side of a user's face.

8. The eyewear according to claim 7, wherein said lens retaining portions extend curvilinearly away from the bridge portion.

9. The eyewear according to claim 4, wherein the temple member adjacent the larger one of said lens retaining portions is smaller than the temple member adjacent the smaller one of said lens retaining portions.

10. Eyewear according to claim 3, further comprising a ventilation opening in said bridge portion having a pair of opposing side walls which are at an angle with respect to the forward direction for directing air flowing through said ventilation opening in a predetermined direction.

* * * * *